United States Patent
Kaboord et al.

(10) Patent No.: US 12,123,814 B1
(45) Date of Patent: Oct. 22, 2024

(54) G- PROTEIN COUPLED RECEPTOR EXTRACTION FORMULATIONS

(71) Applicant: Pierce Biotechnology, Inc., Rockford, IL (US)

(72) Inventors: Barbara Kaboord, Oregon, WI (US); Joanna Geddes, Rockton, IL (US); Christopher Wojewodzki, Rockton, IL (US); Kay Opperman, Oregon, WI (US); Scott Meier, Byron, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 739 days.

(21) Appl. No.: 16/900,019

(22) Filed: Jun. 12, 2020

Related U.S. Application Data

(60) Provisional application No. 62/861,466, filed on Jun. 14, 2019.

(51) Int. Cl.
| | | |
|---|---|---|
| *C07K 1/14* | (2006.01) | |
| *C07K 14/705* | (2006.01) | |
| *C07K 14/72* | (2006.01) | |
| *G01N 1/40* | (2006.01) | |
| C07H 3/04 | (2006.01) | |
| C07J 9/00 | (2006.01) | |
| C07J 41/00 | (2006.01) | |

(52) U.S. Cl.
CPC ........... *G01N 1/4044* (2013.01); *C07K 1/145* (2013.01); *C07K 14/705* (2013.01); *C07K 14/723* (2013.01); *C07H 3/04* (2013.01); *C07J 9/00* (2013.01); *C07J 41/0033* (2013.01); *G01N 2001/4061* (2013.01)

(58) Field of Classification Search
CPC .... C07K 1/145; C07K 14/705; C07K 14/723; G01N 1/4044; G01N 2001/4061
See application file for complete search history.

(56) References Cited

U.S. PATENT DOCUMENTS

| | | | |
|---|---|---|---|
| 6,313,264 B1 * | 11/2001 | Caggiano | G01N 33/68 435/183 |
| 2010/0029917 A1 * | 2/2010 | Von Hagen | C07K 14/705 530/422 |
| 2014/0275487 A1 * | 9/2014 | Steyaert | C07K 14/435 530/391.1 |
| 2016/0054206 A1 * | 2/2016 | Nelson | G01N 1/30 435/40.52 |
| 2017/0166634 A1 * | 6/2017 | Williams | C07K 16/28 |
| 2018/0078468 A1 * | 3/2018 | Jerri | C11D 9/00 |
| 2019/0010523 A1 * | 1/2019 | Walther | C12P 7/42 |

(Continued)

OTHER PUBLICATIONS

Yeliseev et al. Expression of human peripheral cannabinoid receptor for structural studies. Protein Science. 2005, vol. 14, pp. 2638-2653. (Year: 2005).*

(Continued)

*Primary Examiner* — Jeffrey E. Russel

(57) ABSTRACT

Formulations for extraction and stabilization of G-Protein Coupled Receptors (GPCRs), kits and methods for their use for extracting GPCRs from biological specimens (e.g., cells and tissues), and methods for making such formulations in bulk scale are described. GPCRs extracted from cells and tissues using the described formulations remain in a functional, solubilized form over extended time periods.

20 Claims, 10 Drawing Sheets

(56) References Cited

U.S. PATENT DOCUMENTS

2019/0032033 A1\* 1/2019 Carpenter ............... C12N 9/14
2024/0052017 A1\* 2/2024 Henderson ........... C07K 14/723

OTHER PUBLICATIONS

Jappelli et al. Expression and Functional Characterization of Membrane-Integrated Mammalian Corticotropin Releasing Factor Receptors 1 and 2 in *Eschericia coli*. PLOS ONE. Jan. 2014, vol. 9, Issue 1, e84013. (Year: 2014).\*

Bornert et al. Identification of a Novel Protein-Protein Interaction Motif Mediating Interaction of GPCR-Associated Sorting Proteins with G Protein-Coupled Receptors. PLOS ONE. Feb. 2013. vol. 8, Issue 2, e56336. (Year: 2013).\*

Sgro G.G., et al., "Cryo-EM Grid Preparation of Membrane Protein Samples for Single Particle Analysis," Frontiers in Molecular Biosciences, Mini Review, Jul. 31, 2018, vol. 5, Article 74, 8 pages.

Thermo Scientific: "GPCR Extraction and Stabilization Reagent (A43436)," Catalog No. A43436, 2 pages.

\* cited by examiner

G-PROTEIN COUPLED RECEPTOR EXTRACTION FORMULATIONS

CROSS-REFERENCE TO RELATED APPLICATIONS

This application is a Non-Provisional of U.S. Provisional application No. 62/861,466, filed Jun. 14, 2019.

TECHNICAL FIELD

Formulations for extraction and stabilization of G-Protein Coupled Receptors (GPCRs), kits and methods for their use for extracting GPCRs from biological specimens (e.g., cells and tissues), and methods for making such formulations in bulk scale are described.

BACKGROUND

G protein-coupled receptors are a large protein family of receptors that play a key role in transmitting signals across the cell membrane. These receptors are effective drug targets for genetic and immune system disorders and serve as potential biomarkers and therapeutic targets for cancer treatment. Typically, GPCRs are extracted from the cell membrane prior to further downstream biological studies. Most functional GPCR assays must be performed immediately following extraction of the receptor, with activity rapidly degrading over time. The challenges of stabilizing GPCRs in their native and functional form after extraction make studies of these receptors outside of the cell membrane extremely difficult. Thus, there is a need for improved formulations for extracting GPCRs from biological samples and maintaining their stability once extracted from the cell membrane.

SUMMARY

In one aspect, a method is described for preparing a solution in bulk scale that includes a solubilized cholesterol derivative. The method includes combining a first detergent and a second detergent to provide a solution at a first temperature; adding a buffering agent into the solution; elevating the temperature of the solution to a second temperature, wherein the second temperature is greater than the first temperature; mixing greater than 0.1% (w/v) cholesterol derivative into the solution at the second temperature; and adding a polyol into the solution to provide a bulk scale solution that is buffered to pH 5-8, wherein the cholesterol derivative is solubilized in the bulk scale solution. In some embodiments, the first and second detergents can be a non-ionic detergent and a zwitterionic detergent. The method can further include returning the bulk scale solution to a third temperature that is less than the second temperature, wherein the cholesterol derivative is solubilized in the bulk scale solution at the third temperature.

In another aspect, a method is described for preparing a solution in bulk scale that includes a solubilized cholesterol derivative, wherein the method includes combining a non-ionic detergent and a zwitterionic detergent to provide a solution; adding a buffering agent into the solution; mixing greater than 0.1% (w/v) a cholesterol derivative into the solution at elevated temperature; and adding a polyol into the solution to provide a bulk scale solution, wherein the volume of the bulk scale solution is greater than 50 mL and is buffered to pH 5-8, and wherein the cholesterol derivative is solubilized in the bulk scale solution.

In yet another aspect, a method is described for preparing a solution in bulk scale that includes a solubilized cholesterol derivative, wherein the method includes combining 0.1% to 5% (w/v) non-ionic detergent and 0.1% to 1% (w/v) zwitterionic detergent to provide a solution; adding buffering agent into the solution; mixing greater than 0.1% (w/v) cholesterol derivative into the solution at elevated temperature; and adding 10-50% (w/v) polyol into the solution to provide a bulk scale solution, wherein the volume of the bulk scale solution is greater than 50 mL and is buffered to pH 5-8, and wherein the cholesterol derivative is solubilized in the bulk scale solution. In any of the methods provided herein to prepare a bulk scale solution containing solubilized cholesterol derivate, the method can further include cooling the heated solution, such that the cholesterol derivative remains solubilized in the bulk scale solution for up to 2 years.

In yet another aspect, a bulk scale solution is provided that includes solubilized cholesterol derivative prepared according to a method of preparation, as disclosed herein. In some embodiments, the cholesterol derivative remains solubilized in the bulk scale solution when stored at 4° C. for up to 2 years.

In yet another aspect, a bulk scale solution is provided that includes solubilized cholesterol derivative. The solution can include a maltoside-based non-ionic detergent; a zwitterionic detergent; a buffering agent; 10-50% (w/v) polyol; and greater than 0.1% (w/v) cholesterol derivative, wherein the concentration ratio (w/v) of the cholesterol derivative to maltoside-based non-ionic detergent is 0.5 or less, and wherein the solution is at a pH of 5-8 (e.g., 7-7.5), and wherein the cholesterol derivative is solubilized in the bulk scale solution. In another embodiment, the bulk scale solution includes a non-ionic detergent; a zwitterionic detergent; a buffering agent; a cholesterol derivative; and a polyol, wherein the volume of the bulk scale solution is greater than 50 mL and is buffered to pH 5-8 (e.g., 7-7.5), and wherein the cholesterol derivative is solubilized in the bulk scale solution. In yet another embodiment, the bulk scale solution including a solubilized cholesterol derivative includes 0.1% to 5% (w/v) maltoside-based non-ionic detergent; 0.1% to 1% (w/v) zwitterionic detergent; 1-200 mM buffering agent; greater than 0.1% (w/v) cholesterol derivative, wherein the ratio of cholesterol derivative to total detergent is less than 0.5; and 10-50% (w/v) polyol, wherein the volume of the bulk scale solution is greater than 50 mL and is buffered to pH 5-8 (e.g., 7-7.5), and wherein the cholesterol derivative is solubilized in the bulk scale solution.

In any of the methods, kits or solutions provided herein, the non-ionic detergent can be n-dodecyl-b-D-maltopyranoside, n-octyl-β-D-maltopyranoside, n-hexyl-β-D-maltopyranoside, glyco-diosgenin, Fos-choline, lauryl maltose neopentyl glycol, maltose neopentyl glycol, poly(oxy-1,2-ethanediyl), sorbitan monododecanoate (Tween), α-[4-(1,1,3,3-tetramethylbutyl)phenyl]-ω-hydroxy-poly(oxy-1,2-ethanediyl) (Triton), or α-dodecyl-w-hydroxy-poly(oxy-1,2-ethanediyl) (Brij). The zwitterionic detergent can be 3-[(3-cholamidopropyl)dimethylammonio]-1-propanesulfonate (CHAPS), cocamidopropyl hydroxysultaine, cocamidopropyl betaine, phosopholipids, phosphatidylethanolamine, or phosphatidylcholine. The buffering agent can be HEPES (4-(2-hydroxyethyl)-1-piperazineethanesulfonic acid), Tris tris(hydroxymethyl)aminomethane, Bis-Tris, MOPS (3-(N-morpholino)propanesulfonic acid), MES (2-(N-morpholino) ethanesulfonic acid), HEPPs, or PIPES (piperazine-N,N'-bis (2-ethanesulfonic acid). The cholesterol derivative can be cholesteryl hemisuccinate (CHS), cholestrol α-D-glucopyranosyl-(1→4)-β-D-glucyopryanoside (Chobimalt), or 5,11, 17-tris[(carboxy)methyl]-25-monomethoxytriazolo-(3α-cholesteryl)-26,27,28-trihydroxycalix[4]arene (CALXCHOL). In some embodiments, the cholesterol derivative can be an acidic cholesterol ester. The polyol can be glycerol, sorbitol, or xylitol.

Once extracted from the biological specimen, the methods provided herein can further include subjecting the solubilized GPCR to a western blotting assay, wherein the average yield of solubilized GPCR in the lysate supernatant is ≥80% when compared to the insoluble pellet. In some embodiments, the methods provided herein can further include subjecting the solubilized GPCR to a Ligand Binding Assay, wherein the activity of the extracted GPCR is two times greater when compared to the same GPCR extracted in the absence of cholesterol derivative. In some embodiments, the methods provided herein can further include subjecting the solubilized GPCR to a Ligand Binding Assay to show activity being maintained upon storage, wherein greater than 70% of the function of the GPCR is maintained when stored for 7 days upon storage at 4° C. or wherein greater than 70% of the function of the GPCR is maintained when stored for 1 month upon storage at −20° C.

In yet another aspect, a method of extracting a membrane protein from a cell or a tissue is provided that includes providing a sample that includes a cell or a tissue; and incubating the sample in the extraction solution disclosed herein, wherein the solution is in an amount sufficient to extract the membrane protein from the cell or tissue, and wherein the extracted membrane protein is solubilized in the solution. The membrane protein can be a G-protein coupled receptor (GPCR), and the solubilized GPCR can maintain functional integrity. In some embodiments, wherein greater than 70% of the function of the GPCR is maintained when stored for 7 days at 4° C. or wherein greater than 70% of the function of the GPCR is maintained when stored for 1 month at −20° C.

In yet another aspect, a kit for extracting a GPCR from a cell or tissue is provided that includes: a) the extraction solution, as described herein; and b) instructions for extracting the GPCR from the cell or tissue. In any of the methods, solutions or kits provided herein, the cholesterol derivative can be solubilized in the bulk scale solution after storage at 4° C. for 1 month or greater. In some embodiments, the bulk scale solution can have a volume of 50 mL or greater. In other embodiments, the volume of bulk scale solution is 1 L or greater.

DETAILED DESCRIPTION

Figure 1:
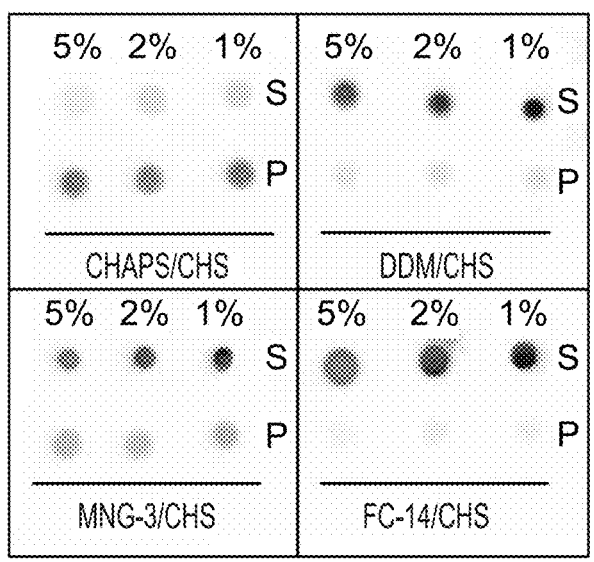
FIG. 1 shows an immunodot blot image for receptors extracted from CHO-K1 cells transfected with CXCR4-eGFP and M3-eGFP using CHAPS, DDM, MNG-3 and FC-14 buffers at different concentrations in combination with cholesterol hemisuccinate (CHS).
Figure 1:
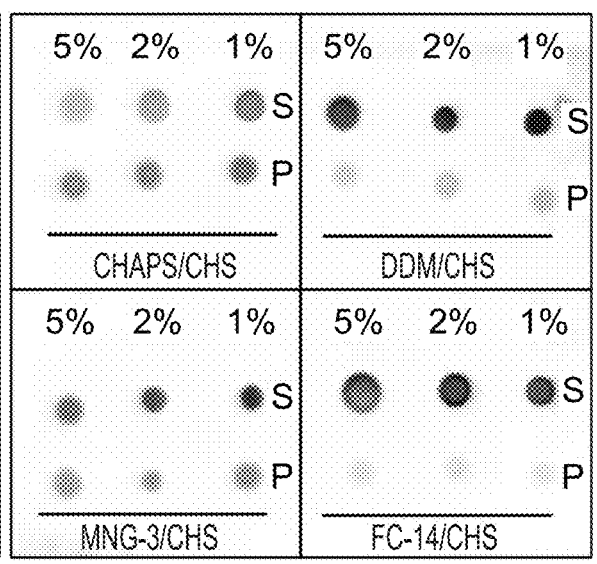

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "about", when used to describe a numerical value, encompasses a range up to #15% of that numerical value, unless the context clearly dictates otherwise.

While compositions and methods are described in terms of "comprising" various components or steps (interpreted as meaning "including, but not limited to"), the compositions and methods can also "consist essentially of" or "consist of" the various components and steps, such terminology should be interpreted as defining essentially closed-member groups.

"G-protein coupled receptor" or "GPCR," as used herein, refers to a family of receptors that are 7TM proteins and play a key role in transmitting signals across the cell membrane. GPCRs consist of a single polypeptide that is folder into a globular shape and embedded in the plasma membrane of a cell. Representative, non-limiting, examples of GPCRs that are suitable for extraction from cells and tissues using the described extraction formulation include 5HT1A, GPR120, mGluR3, B2AR, A2AR, M3, Thrombin Receptor, PAR1, CXCR4, and CALCR.

"Biological specimen" or "biological sample," as used herein, refers to hematological, cytological and histological specimens, such as cells, 3D cell cultures (e.g. spheroids and organoids), tissues, whole organisms (e.g. flies, worms, zebrafish), cell-free extracts, or a fluid sample (e.g., blood or sputum). A tissue specimen can be any type of nervous, epithelial, muscular, and connective tissue, including an organ tissue. Biological samples can be from a plant or animal (e.g., human, mouse, fly, worm, fish, frog, fungi, and the like).

"Solubilization," as used herein, refers to the process of incorporating a membrane bound protein into a detergent micelle. "Solubilization" also refers to the process of incorporating a component into a solution. As used herein, "dissolution" is used interchangeably with the term "solubilization." Membrane bound proteins (e.g., GPCRs) are considered "solubilized" if incorporated into detergent micelles. A component is considered "solubilized" if incorporated into a solution to such an extent that there are no visible particulates in the solution. As used herein, "dissolved" is used interchangeably with the term "solubilized."

In general, formulations for use in extracting membrane bound proteins from a biological specimen are described herein, including, but not limited to, receptor and transporter proteins. The disclosed formulations can maintain the membrane bound protein in solution in a functional form. A particularly important class of membrane bound proteins that can be extracted using the disclosed formulations is the class of receptors referred to as GPCRs. In one aspect, the formulations described herein are effective for extracting a GPCR from the membrane of a cell or tissue sample. The GPCR extraction formulation described herein efficiently solubilizes the GPCR and stabilizes the receptor in solution, allowing researchers to investigate the structure and function of these receptors outside of the cell. For example, GPCRs solubilized with the described extraction formulation can be stored in the solution for up to a month or greater. In addition, extracted GPCRs can be stored in the formulation at temperatures that are routinely used for storing buffers (e.g., 4° C. to −20° C.) with minimal loss of function. GPCR stability has been verified using both overexpressed and endogenous receptors and assayed by western blot and receptor-ligand binding assays. Thus, the formulations provided herein allow for improved extraction efficiency, solubility and preserved activity. The improved performance of the described extraction formulations can facilitate greater flexibility in the type of GPCR research and targeted therapeutic studies that can be conducted.

The formulations provided herein include a combination of components selected to optimize extraction of the membrane bound protein from the cell membrane and provide for solubilization of the extracted membrane bound protein in detergent micelles. The extracted proteins are solubilized in native (i.e., functional) form and remain solubilized in functional form over extended periods of time. GPCRs are one class of membrane bound proteins that can be extracted and stabilized using the disclosed formulations. Although specific reference is made to GPCRs herein, it should be understood that the extraction formulations provided herein can be used for the efficient extraction and stabilization of any type receptor or transporter protein, including, but not limited to, GPCRs.

The extraction formulations described herein include one or more components effective for the extraction of a membrane bound protein (e.g., GPCR) from the membrane of a cell. Thus, formulations provided herein include one or more components, such as a detergent, that facilitate efficient extraction of the GPCR from the cell or tissue. Applicant has discovered that a formulation that includes a combination of detergents can increase incorporation of the extracted protein in the detergent micelle as compared to formulations that implement only a single type of detergent. In particular, a combination of non-ionic and zwitterionic detergents, in the presence of a component that aids in the stabilization of the protein in functional form, have been found to be particularly effective for solubilization of the extracted membrane bound protein from cell membranes into detergent micelles. Representative examples of non-ionic detergents include maltoside-based non-ionic detergents, such as, n-dodecyl-b-D-maltopyranoside, n-octyl-β-D-maltopyranoside, lauryl maltose neopentyl glycol, maltose neopentyl glycol, and n-hexyl-β-D-maltopyranoside. Other suitable examples of non-ionic detergents include glyco-diosgenin, Fos-choline, poly(oxy-1,2-ethanediyl), sorbitan monododecanoate (Tween), α-[4-(1,1,3,3-tetramethylbutyl)phenyl]-ω-hydroxy-poly(oxy-1,2-ethanediyl) (Triton), and α-dodecyl-w-hydroxy-poly(oxy-1,2-ethanediyl) (Brij). Typically, the extraction formulation includes about 0.1% to about 5% (w/v) of a non-ionic detergent (e.g., maltoside-based non-ionic detergent). The extraction formulations described herein can further include a zwitterionic detergent. Among other advantages, incorporation of a zwitterionic detergent in the formulation can improve the solubility of the stabilizer (e.g., a cholesterol derivative) in the formulation. Representative examples of zwitterionic detergents that can be included in the disclosed formulations include 3-[(3-cholamidopropyl)dimethylammonio]-1-propanesulfonate (CHAPS), cocamidopropyl hydroxysultaine, cocamidopropyl betaine, phosopholipids, phosphatidylethanolamine, and phosphatidylcholine. In some embodiments, the extraction formulation includes about 0.1% to 1% (w/v) zwitterionic detergent.

The extraction formulation can include a cholesterol derivative to provide for stabilization of the extracted protein in the detergent micelle. In certain embodiments, the cholesterol derivative is an acidic cholesterol ester (e.g., CHS). Representative examples of cholesterol derivatives useful for stabilization of extracted GPCRs include cholesteryl hemisuccinate (CHS), cholestrol α-D-glucopyranosyl-(1→4)-β-D-glucyopryanoside (Chobimalt), and 5,11,17-tris[(carboxy)methyl]-25-monomethoxytriazolo-(3α-cholesteryl)-26,27,28-trihydroxycalix[4]arene (CALXCHOL). The formulation typically includes greater than 0.1% (w/v) of the cholesterol derivative. In some embodiments, the formulation can include about 0.1% to 0.5% (w/v) of the cholesterol derivative. In certain embodiments, the formulation includes about 0.15% to 0.3%. (w/v) of the cholesterol derivative. In certain embodiments, the formulation includes about 0.2% (w/v) of the cholesterol derivative.

The ratio of cholesterol derivative to total detergent (i.e., the combination of non-ionic and zwitterionic detergents) in the formulation can be tailored to achieve optimal extraction efficiency and stabilization of the extracted GPCR. In certain embodiments, formulations with a ratio of cholesterol derivative to total detergent that is 0.5 or less (w/v) provides optimal performance for the extraction and stabilization of GPCRs. In certain embodiments, the ratio of cholesterol derivative to total detergent (w/v) is less than 0.4; or less than 0.3; or less than 0.2. In some embodiments, ratio of cholesterol derivative to total detergent (w/v) is 0.1 to 0.19 (e.g., 0.1 to 0.15:0.1 to 0.16:0.1 to 0.17; or 0.1 to 0.18).

One or more additional components can be included in the formulation to improve the efficiency of extraction, increase yield of extracted GPCRs, aid in the solubilization of the cholesterol derivative, maintain the stability of the formulated buffer at a bulk scale, and/or enhance the shelf life of the formulations. For example, certain formulations can include an additional component(s) to maintain the cholesterol derivative in solution under extended storage conditions and at reduced temperature. In certain embodiments, the cholesterol derivative remains fully solubilized in the solution even after extended storage times and at reduced temperature (e.g., 4° C.). Exemplary components that can be included in the formulation to improve stability of the cholesterol derivative in solution include polyols, i.e. a compound having two or more hydroxyl groups. Polyols useful in the described extraction formulations typically have less than 10 hydroxyl groups. In certain embodiments, the polyol has less than 7 hydroxyl groups, such as, e.g., glycerol, sorbitol, or xylitol. In certain embodiments, a combination of polyols can be included in the formulation. Applicant has discovered that addition of a sufficient concentration of a polyol into an extraction formulation that includes a cholesterol derivative and a combination of zwitterionic and non-ionic detergents, as described herein, can significantly reduce the amount of cholesterol derivative that precipitates out of solution after storage at reduced temperature. Thus, formulations are provided herein for the efficient extraction and stabilization of GPCRs in functional form from a biological specimen that include a polyol. The amount of polyol in the formulation can be adjusted to the extent needed for maintain the components in a fully dissolved (i.e., solubilized) form in the formulation. Applicant discovered that it can be beneficial to use about 10% or greater (w/v) polyol in the formulation to help maintain the CHS in solution. Typically, the extraction formulation includes about 10-50% (w/v) polyol (e.g., 10%-20%; or 20%-30%; or 30%-40%; or 40%-50% (w/v)).

Formulations described herein can further include additional components, such as, e.g., preservatives, to prevent degradation of the formulation during prolonged storage and/or to prevent or minimize bacterial growth. Suitable preservatives include, e.g., sodium benzoate, benzoic acid or sodium azide, and are typically present in the formulation at a concentration of less than 2% by weight. Additional components, such as metal chelators (e.g., EDTA) and salts (e.g., NaCl and $MgCl_2$) also can be included to provide formulations in physiological conditions.

Extraction formulations disclosed herein also can include a buffering agent to maintain the pH of the formulation at biologically-relevant levels. Typically, the formulation is most effective at extracting and solubilizing GPCRs when buffered to a pH of about 5 to 8. In certain embodiments, the pH of the buffer is adjusted to about 6-8. In other embodiments, the pH of the buffer is adjusted to about 7-7.5. To maintain the pH for optimal performance, the extraction formulation typically includes about 1-200 mM of a buffering agent. In certain embodiments, the buffering agent can be a zwitterionic organic buffering agent. Representative examples of buffering agents include zwitterionic buffering agents, such as, HEPES (4-(2-hydroxyethyl)-1-piperazineethanesulfonic acid), Tris tris(hydroxymethyl)aminomethane, Bis-Tris, MOPS (3-(N-morpholino)propanesulfonic acid), MES (2-(N-morpholino)ethanesulfonic acid), HEPPs, and PIPES (piperazine-N,N'-bis(2-ethanesulfonic acid).

With the growing interest in large-scale GPCR screening of biomarkers and drug targets, among other applications, there is a need for large-scale production of extraction buffers. Cholesterol derivatives for the extraction of GPCR's from cells and tissues typically are formulated into buffers on a relatively small laboratory scale (e.g., less than 50 mL) using a probe sonicator to solubilize the cholesterol derivative and freshly used in down-stream biological applications. Even at small R&D scales, cholesterol derivatives used in such formulations (e.g., CHS) can be difficult to solubilize and often do not remain fully solubilized in the solution for extended periods of time. GPCR extraction formulations can become cloudy over time indicating separation and/or precipitation of the cholesterol derivative. Applicant has found that sonication methods for solubilizing cholesterol derivatives do not scale with larger volumes of solution, and the problem of unsolubilized cholesterol derivatives becomes particularly problematic for volumes of solution exceeding 1 L. To date, there has been no viable approach for preparing large volumes (e.g., 1 L or greater) of GPCR extraction formulations that are shelf-stable and maintain the cholesterol derivative in a solubilized form for extended periods of time. A particular advantage of the extraction formulations provided herein is that the cholesterol derivative and other components remain solubilized in the buffer, even when prepared at bulk scale and when stored for an extended period of time (e.g., from weeks to several years). Because the formulations are shelf stable and can be effectively used for the extraction of GPCRs from biological specimens despite prolonged storage, the formulations provided herein are particularly practical for those wanting to prepare and store large volumes of extraction buffer for future down-stream applications.

Bulk scale formulations described herein include one or more detergents for solubilizing GPCRs from the cell membrane. In certain embodiments, the bulk scale formulation includes two different detergents. The detergent(s) contribute to the extraction of the GPCR from the cell membrane. In certain embodiments, the formulation includes a non-ionic detergent (e.g., DDM) for the extraction of the GPCR from the cell membrane. The detergent(s) can form micelles that encapsulate the extracted GPCR. The formulation can further include component(s) for efficient stabilization of GPCRs in detergent micelles. In certain embodiments, the bulk scale formulation includes a cholesterol derivative for stabilizing the GPCRs in functional form. Cholesterol derivatives (e.g., CHS) are generally very difficult to solubilize in aqueous solution at room temperature. Incorporation of a zwitterionic detergent (e.g., CHAPS) into the bulk scale formulation can significantly improve the solubility of the cholesterol derivative. Although zwitterionic detergents have been contemplated for extraction of GPCRs from cell membranes, this class of detergents was found to not be sufficient for high yield extractions of the GPCR from the cell membrane in the absence of a non-ionic detergent. Thus, provided herein are bulk scale formulations that utilize a combination of a non-ionic (e.g., a maltoside-based) detergent, a zwitterionic detergent and a cholesterol derivative. It was discovered that addition of a polyol into the formulation in a sufficiently high concentration (e.g., 10% w/v or greater) further contributes to solubilizing the cholesterol derivative in bulk scale solution, even after extended storage times.

Thus, provided herein are bulk scale formulations for the extraction of GPCRs from biological specimens. In certain embodiments, the volume of the bulk scale formulation is greater than 50 mL (e.g., 100 mL or greater). In certain embodiments, the volume of the bulk scale formulation is about 1 L or greater (e.g., 1 L-10 L; or 10 L-25 L; or 25 L-50 L; or 50 L-75 L; or 75 L-100 L). In certain embodiments, the volume of the bulk scale formulation is about 1 L to about 25 L).

Bulk scale extraction formulations described herein are stable for an extended period of time. Stable formulations include components that remain solubilized in the solution and do not separate or precipitate over time. The extent to which components are solubilized in the solution can be assessed by visual inspection (e.g. assessing for cloudiness or the presence of white particulate in the sample) and/or can be determined using appropriate instrumentation and/or with functional testing using techniques that are well known in the art.

Formulations are provided herein in which the components remain solubilized in the formulation for greater than 1 year (e.g., up to 2 years; or up to 3 years) when stored at or below room temperature (e.g., 4° C.-20° C.). A significant advantage of the bulk scale formulations is that the cholesterol derivative remains solubilized and available for efficient stabilization of extracted GPCRs. In certain embodiments, an extraction formulation is provided that includes solubilized acidic cholesterol ester that remains solubilized in the buffer when stored at 4° C. for up to 2 years. Because the cholesterol derivative and other components remain solubilized in the buffer, the formulations disclosed herein offer a practical advantage in that a large volume of the formulation can be prepared and then stored for an extended period of time, and used as needed. In addition, the formulations disclosed herein include a combination of components that efficiently extract GPCRs from cell membranes in high yield and in a functional form suitable for use in down-stream applications. Extracted GPCRs remain solubilized in the formulations for extended periods of time under conditions typically used to store biological samples and buffers. For example, GPCRs extracted from a biological specimen using the described formulations typically retain greater than about 70% of their function when stored for 7 days at 4° C. or for 1 month at −20° C.

Also provided herein are novel methods of preparing an extraction formulation including solubilized cholesterol derivative in bulk scale. A representative method for preparing the extraction formulation is set forth in the process depicted in FIG. 8. The method includes combining two different detergents, e.g., a non-ionic detergent and zwitterionic detergent, as described herein, to provide a solution. In some methods, the detergents can be combined with continuous mixing. For example, the solution can be prepared in a large reaction vessel (e.g., round-bottom flask) fitted with a mechanism for stirring the solution. The solution is mixed, e.g., using an overhead stir unit to facilitate solubilization of the solution components. Typically, mixing speeds of less than 1000 rpm are used to avoid undue agitation. A buffering agent, as described herein, then is added into the solution with stirring. The amount of buffering agent added is sufficient to maintain the pH of the solution at about 5-8. In some embodiments, the pH of the solution is maintained at about pH 7-7.5. The solution then is heated to an elevated temperature, and the cholesterol derivatives is added to the heated solution with continuous stirring until the cholesterol derivative is fully solubilized in the solution. In some embodiments, the reaction vessel is surrounded with a heating mantle to evenly heat the contents of the reaction vessel, and the temperature is regulated using, e.g., a temperature controller. The heating temperature can be adjusted to maximize solubilization of the components in the formulation. Typically, the heating temperature can range from about 40° C.-100° ° C. In some embodiments, the heating temperature is greater than about 70° C. (e.g., about 80° C. to about 90° C.). Once the solution has been heated to the desired temperature, the cholesterol derivative is added into the solution with continuous stirring. In certain embodiments, greater than 0.1% (w/v) cholesterol derivative is added into the solution. Depending on the temperature used for heating the solution, the cholesterol derivative can be solubilized in the solution within several hours or less. For example, the cholesterol derivative can be solubilized in the solution within just 30 minutes to 1 hour when added to a solution heated to about 80° C. After the cholesterol derivative is solubilized in the solution, the solution can be removed from the heating source, allowed to cool slightly, and a sufficient quantity of polyol, as described herein, is added to the solution. Once all components are combined, the total volume of the bulk solution is greater than 50 mL. In some embodiments, the bulk solution can be prepared at volumes of 1 L or greater (e.g., 10 L or greater; or 20 L or greater).

Another representative method for preparing a solution in bulk scale in which cholesterol derivative is solubilized includes combining a first detergent and a second detergent to provide a solution. A buffering agent is added to the solution to buffer the solution to a pH of 5-8. Then, the solution is heated and greater than 0.1% (w/v) cholesterol derivative is mixed into the heated solution. Once the cholesterol derivative is solubilized in the heated solution, a polyol is added. The heated solution can be returned to a lower temperature (e.g., room temperature or below). Surprisingly, the cholesterol derivative remains solubilized in the bulk scale solution even when temperatures are below room temperature and over extended storage times.

Yet another representative method for preparing the extraction formulation in bulk scale includes combining 0.1% to 5% (w/v) non-ionic detergent and 0.1% to 1% (w/v) zwitterionic detergent to provide a solution. 1-200 mM of a buffering agent then is added into the solution to maintain the pH to about 5-8. In some embodiments, the pH of the solution is maintained at pH 7-7.5. The solution then is heated to an elevated temperature, and greater than 0.1% (w/v) cholesterol derivative is mixed into the solution with continuous stirring until the cholesterol derivative is fully solubilized in the solution. 10-50% (w/v) polyol then is added to the solution removed from heat. The solution is allowed to return to ambient temperature (e.g., room temperature or below) and stored for later use. As described herein, the components of the solution remain solubilized in the solution despite extended storage times at room temperature or less.

The methods described herein implement a combination of heating and mixing to fully dissolve the cholesterol derivative in the formulation. Thus, the methods described herein for preparing bulk scale extraction formulations differ from methods for preparing extraction buffers at laboratory scale (<50 mL) that rely on sonication to solubilize the cholesterol derivatives. It was found that methods implementing sonication were not effective at dissolving cholesterol derivatives when the formulation was prepared in bulk scale and contained significant unsolubilized cholesterol derivative remaining despite extended periods of sonication (see, Example 5).

Thus, provided herein is a novel method for preparing shelf stable formulations at bulk scale that include components for both extracting and stabilizing GPCRs in soluble, functional form, all in one formulation. Because the formulation includes components for both the extraction and stabilization, the described formulations simplify isolation of GPCRs from biological samples compared to existing methods in the art, where extraction of GPCRs from cells or tissue and stabilization of the extracted GPCRs are conducted in separate steps. The use of the described formulations for extraction significantly decreases the complexity and sample processing time associated with workflows involving separate extraction and stabilization steps.

The methods described herein can be used to prepare formulations that include components to 1) efficiently extract GPCRs from cell membranes in high yield, and 2) stabilize the extracted GPCRs in a soluble and biologically functional form, such that the GPCR can be interrogated in further down-stream assays.

Functional performance can be interrogated using assays that are well known to those skilled in the art, including, but not limited to, Western blotting, immunoprecipitation/purification, ligand receptor binding assays, surface plasmon resonance (SPR) and structural studies. For example, the extent of solubilized functional GPCR can be assessed using western blotting techniques. In one representative method, the solubilized GPCR is subjected to a Western Blotting Assay, as described herein, wherein the average yield of solubilized GPCR in the lysate supernatant is ≥80% when compared to the insoluble pellet. In another method, the extent of GPCR function can be assessed using specific ligand binding techniques. For example, the functional integrity of the extracted GPCR can be assessed by comparing buffers formulated with and without cholesterol derivative for stabilization of the solubilized GPCR in radioligand binding assays. Functionality of the receptor can be determined by incubating the solubilized GPCR extract with a radio-labeled ligand specific for the receptor. After incubation, excess ligand is removed and bound ligand is determined. Specific activity is confirmed using a competition reaction of radio-labeled ("hot") ligand to excess non-radioactive ("cold") ligand. "Hot ligand" and "cold ligand," as used herein, refers to a radiolabeled ligand or untagged ligand, respectively, used in radioligand binding assays to determine total receptor activity. When comparing specific receptor ligand binding to the extracted GPCR in buffers prepared with and without cholesterol derivative, a two fold increase in activity in the presence of cholesterol derivative was observed (see, Example 4). Thus, a receptor is considered "active" when the GPCR shows about 50% or greater specific binding to the ligand. An advantage of using the disclosed formulations for extraction of GPCRs from biological specimens is that the functional integrity of the GPCR can be maintained even after prolonged storage times (e.g., up to several months or greater) and after storage at or below room temperature (e.g., at 4° C. or less), as is typically employed for storage of materials used in biological applications. In some embodiments, greater than 50% (e.g., 60% or greater; 70% or greater; or 80% or greater) of the function of the GPCR is maintained after storage for 7 days at 4° C. or when stored for 1 month at −20° C., as determined by a radioligand binding assay.

In another aspect, the formulations provided herein can be used to extract membrane proteins (e.g., GPCRs) in stabilized form from a biological sample. Any suitable biological sample can be evaluated using the methods disclosed herein, including, but not limited to adherent or suspension-based cell samples and tissue samples. In certain embodiments, the sample includes cells or a digested cells and fragments thereof or a 3D cell culture (spheroid/organoid). Because the provided formulations can provide extracted GPCRs in active form, the GPCRs can be investigated using a variety of biological assays known to those skilled in the art. For example, the GPCRs can be utilized in assays for screening biomarkers, therapeutic agents, and drug targets. Post extraction targets also can be purified and interrogated in structural studies using techniques including, e.g., X-ray crystallography, NMR spectroscopy, mass spectrometry, or electron microscopy (e.g, cyro-EM).

In yet another aspect, a method of purifying an extracted membrane protein from an expression cell line is provided that includes providing a sample that includes an expression cell line; and maintaining the sample in one tenth strength of the extraction solution disclosed herein, wherein the solution is in an amount sufficient to maintain the critical micelle concentration required for stabilizing the membrane protein from the expression cell line, and wherein the purified membrane protein is stabilized in the solution. The membrane protein can be a G-protein coupled receptor (GPCR), and the purified GPCR can maintain functional integrity. In some embodiments, the GPCR can be co-expressed and/or co-purified with a G-protein. In some embodiments, the activity of the purified GPCR is greater than the activity of the GPCR in the whole cell lysate when comparing the same protein amounts.

Further provided herein are kits for extracting a GPCR from a cell or tissue. A representative example of a kit for extracting a GPCR from a cell or tissue includes an extraction solution, as described herein, and instructions for extracting a GPCR from a cell or tissue. Additional components can be included in the kit, such as, e.g., components useful for conducting structural studies and/or screening assays, as described herein.

The following examples are included to demonstrate certain embodiments of the invention. It should be appreciated by those of skill in the art that the techniques disclosed in the examples which follow represent techniques discovered by the inventor(s) to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

The examples provided herein utilize the following materials and general methods unless indicated otherwise. Materials were obtained from the following commercial sources: Dodecyl Maltoside (DDM), CHAPS detergent, HEPES buffer, BSA, Pierce BCA Protein Assay Kit, Pierce Bovine Serum Albumin Standards, 10× Tris-Glycine Running Buffer, 1-Step Fast Transfer Buffer, Anti-GFP, Anti-MGluR3, Anti-GPR120, Anti-5HT1A, Anti-Thrombin Receptor, Goat Anti-Rabbit HRP Conjugate, SuperSignal West Dura Substrate Extrended Duration Substrate, 20×TBS Tween™-20 Buffer, Non-Reducing Lane Marker Sample Buffer, DTT, Novex™ 4-20% Tris-Glycine Plus Midi Gel, Zeba Spin Desalting Columns, T-PER Tissue Protein Extraction Reagent, Mem-PER Plus Membrane Protein Extraction Kit, RIPA Lysis and Extraction Buffer, Scintillation Cocktail, GeneBLAzer M3-NFAT-bla CHO-K1 Cells, CXCR4-cGFP or M3-eGFP cell lines (all from Thermo Fisher Scientific (Waltham, MA)). Fos-Choline 14 detergent (FC), Lauryl Maltose Neopentyl Glycol (MNG-3), Cholesteryl Hemisuccinate Tris Salt (CHS), and 10:1 DDM/CHS Pre-made Solution from Anatrace (Maumee, OH). HCT116, HeLa, HEK293 Pel-Freez Biologicals: Mouse Brain Stripped, Mouse Liver were from ATCC (Manassas, VA). ProteoExtract Transmembrane Protein Extraction Kit and poly (ethylene glycol) diamine from Sigma-Millipore (St. Louis, MO). 4-DAMP Methyl 3H from Perkin Elmer (Waltham, MA) and Ipratropium Bromide from Tocris (Bristol, UK).

Membrane Protein Extraction: $1 \times 10^7$ cultured cells or 50-100 mg of tissue are washed in PBS and subsequently mechanically lysed in 1 mL of a hypotonic buffer, followed by an incubation at 4° C. for 15 minutes. Samples are then centrifuged at 16,000×g for 20 minutes. The supernatant containing the cytosolic proteins is removed, and the pellet is resuspended in extraction reagent to solubilize membrane proteins, and incubated for 30-60 minutes at 4° C. After a second centrifugation at 16,000×g for 20 minutes the supernatant containing the membrane proteins is collected. The remaining pellet is then resuspended in 1 mL of RIPA Lysis Reagent and sonicated for 10 seconds at 50% Amps. Extractions using commercially available kits are performed according to provided product manual. Protein in each fraction is estimated using the BCA Assay Kit.

Whole Cell Protein Extraction: $1 \times 10^7$ cultured cells or 50-100 mg of tissue are washed in PBS and subsequently lysed in 1 mL Extraction Reagent, and incubated for 30-60 minutes at 4° C. After incubation samples are centrifuged at 16,000×g for 20 minutes. The supernatant containing the solubilized protein is collected. The remaining pellet is then resuspended in 1 mL of RIPA Lysis Reagent and sonicated for 10 seconds at 50% Amps. Extractions using commercially available reagent are performed according to provided product manual. Protein in each fraction is estimated using the BCA Assay Kit.

Immunodot Blot Assay: Protein samples are directly applied to a nitrocellulose membrane. Membranes are then blocked with BSA, incubated in primary antibody, washed 5×5 minutes in 1×TBST, incubated in secondary antibody for 30 minutes at room temperature, washed 5×5 minutes in 1×TBST, and incubated for 5 minutes in SuperSignal™ West Dura Extended Duration Substrate (Thermo Scientific). Blots are then imaged on an iBright™ Imaging System (Thermo Scientific).

Western Blot Assay: Normalized samples are separated on a 4-20% Tris Glycine gel and transferred to nitrocellulose membrane using the Pierce G2 Fast Blotter (Thermo Scientific). Membranes are then blocked, incubated in primary antibody, washed 5×5 minutes in 1×TBST, incubated in secondary antibody for 30 minutes at room temperature, washed 5×5 minutes in 1×TBST, and incubated for 5 minutes in SuperSignal™ West Dura Extended Duration Substrate. Blots are then imaged on the iBright™ Imaging System.

Radioligand Binding Assay: M3 extracts diluted in radioligand binding buffer (25 mM HEPES/150 mM NaCl/2% glycerol/1 mM EDTA/0.1% BSA/0.05% DDM/0.001% CHS) to a final concentration of 400 μg are incubated with 4-DAMP Methyl 3H (hot ligand) alone or a competition of Ipratropium Bromide (cold ligand) and 4-DAMP Methyl 3H for 75 minutes at room temperature. Free radioligand is then removed using gel filtration and samples are added to scintillation vials containing 2 mL scintillation fluid, and read on a TRI-CARB 2000 TR scintillation counter (Perkin Elmer). A2AR-GFP-His whole cell lysate, flow-through and purified eluate diluted in radioligand binding buffer (25 mM HEPES/150 mM NaCl/2% glycerol/1 mM EDTA/0.1% BSA/0.05% DDM/0.001% CHS) to a final concentration of 5 μg were incubated with Adenosine 3H (hot ligand) alone or a competition of unlabeled Adenosine (cold ligand) and Adenosine 3H for 75 minutes at room temperature. Free radioligand was then removed using gel filtration and samples were added to scintillation vials containing 2 mL scintillation fluid, and read on a TRI-CARB 2000 TR scintillation counter (Perkin Elmer).

Example 1

Comparison of Extraction Formulations

A series of buffers were prepared using different detergents (CHAPS, DDM, MNG-3 and FC-14) at varying ratios (1%, 2% and 5% w/v) and 2% w/v cholesterol derivative (CHS). In addition, solubilization methods and stabilizing reagents were assessed in the buffer formulation. The buffers were used to extract receptors from CHO-K1 cells transfected with CXCR4-eGFP and M3-eGFP, respectively. Extraction efficiency was determined with the Immunodot Blot Assay using an Anti-GFP antibody by comparing signal intensities for each receptor at each of the concentrations tested (see, FIG. 1). The buffers formulated with FC-14 and DDM yielded efficient extraction when comparing the signal generated from the extracted receptor in the soluble fraction (S) and the insoluble pellet (P). The buffer formulated with MNG showed the majority of both expressed receptors in the soluble fraction (S), with some left behind in the pellet (P). The buffer including CHAPS was unable to efficiently solubilize the overexpressed receptors. In addition, decreasing the percentage of detergent relative to cholesterol derivative resulted in an increased amount of receptor in the soluble fraction. DDM, MNG, and FC-14 samples all showed increased intensity of CXCR4 in the soluble fraction when decreasing from 5-1% detergent. CHAPS, MNG, and FC-14 showed similar results with extracted M3.

Figure 2:
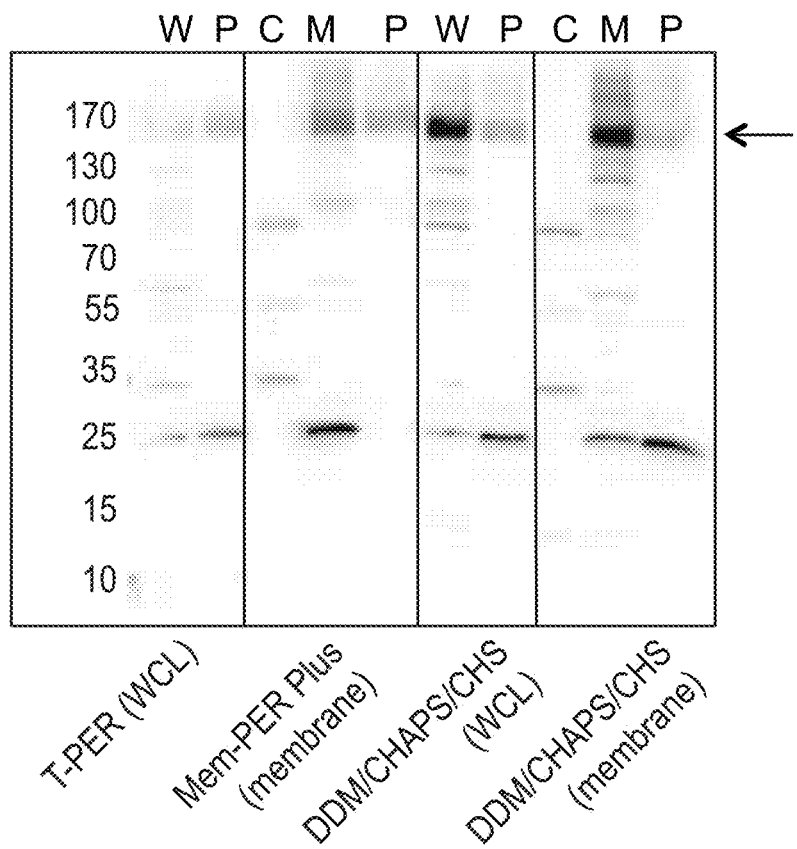
FIG. 2 shows a western blot image for whole cell lysate (WCL) and membrane protein extractions of MGluR3 from mouse brain tissue using an extraction buffer prepared with a combination of 1% DDM, 0.5% CHAPS, and 0.2% CHS, T-PER Reagent, or the Mem-PER Plus Kit.

Whole cell lysate (WCL) and membrane protein extractions from mouse brain tissue were prepared as stated in the above methods using an extraction buffer prepared with a combination of 1% DDM, 0.5% CHAPS, and 0.2% CHS, T-PER Reagent, or the Mem-PER Plus Kit. Extraction efficiency of MGluR3 was determined by comparing signal intensities on a Western blot of the two different extraction methods (membrane protein extraction vs. whole cell lysate) normalized to 10 μg total protein/well (see, FIG. 2). When comparing the fraction with solubilized receptor (W or M) to insoluble fraction (P), buffer formulated with DDM/CHAPS/CHS exhibits superior extraction efficiency of MGluR3 with both whole cell and membrane protein extraction methods. In addition, similar band intensities are seen when directly comparing the two methods with the DDM/CHAPS/CHS buffer indicating that enrichment using the membrane preparation provided no particular advantage.

Example 2

Formulations with Polyol

Figure 3:
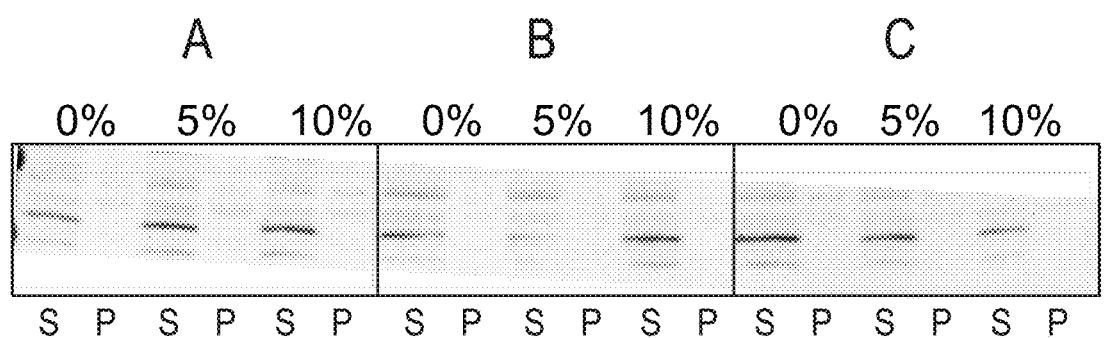
FIG. 3 shows a Western blot image for Formulations A-C using different concentrations of polyol, as described in Example 2.

Formulations A (25 mM HEPES/1% DDM/0.5% CHAPS/0.2% CHS/2 mM EDTA/150 mM NaCl/8 mM MgCl2), B (25 mM HEPES/1% DDM/0.5% CHAPS/0.2% CHS/2 mM EDTA/300 mM NaCl/2 mM $MgCl_2$), and C (25 mM HEPES/1% DDM/0.5% CHAPS/0.2% CHS/2 mM EDTA/150 mM NaCl/16 mM $MgCl_2$) were prepared using a polyol at a concentration of 0%, 5% and 10% (w/v). The formulations were used to extract Free Fatty Acid Receptor 4 (GPR120) expressed endogenously in HCT116 according to the whole cell protein extraction method described in Example 1. Results were analyzed by Western blot comparing the amount of receptor in the soluble fraction (S) and insoluble pellet (P) at each of the concentrations tested. Referring to FIG. 3, the addition of polyol had little effect on extraction efficiency of the receptor. The slight differences that are seen in the band intensity of the soluble fraction may be due to transfer efficiency. However, when the polyol concentration fell below 10%, particulate was visually detected after storage at 4° C., indicating that CHS failed to remain soluble in the formulation.

Example 3

Western Blot Analysis of G Protein-Coupled Receptors

Figure 4A:
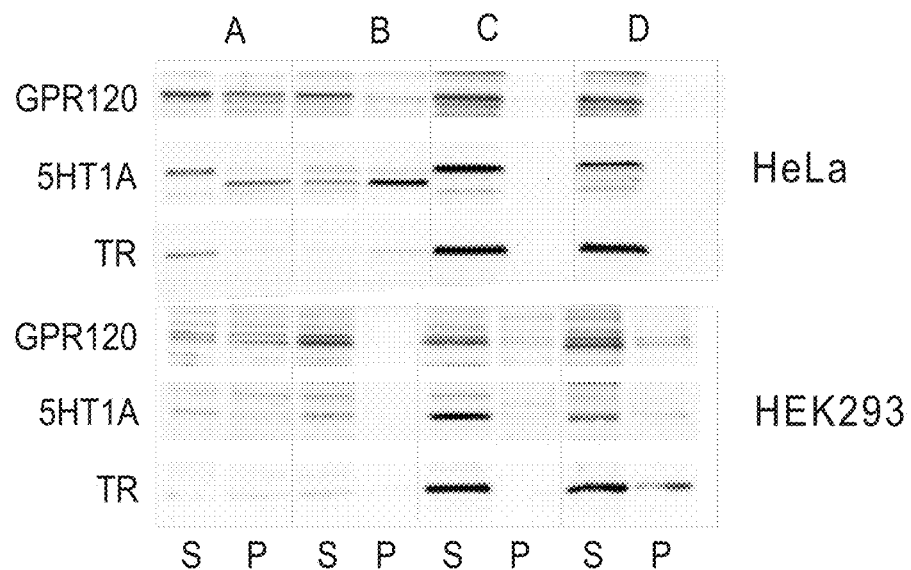
FIG. 4A shows a western blot image for different G protein-coupled receptors (Free Fatty Acid Receptor 4 (GPR120), Serotonin Receptor (5HT1A), and Thrombin Receptor (TR) extracted from human cell lines (HeLa and HEK293) by fractionation using the ProteoExtract Transmembrane Protein Extraction Kit (Millipore) using both buffer options (A & B) and whole cell methods (GPCR extraction reagent (C)) and Thermo Scientific RIPA Lysis reagent (D). The data show that the GPCR extraction reagent (C) provides improved banding and yield in the soluble fraction (S) when compared to the insoluble pellet (P).
Figure 4B:
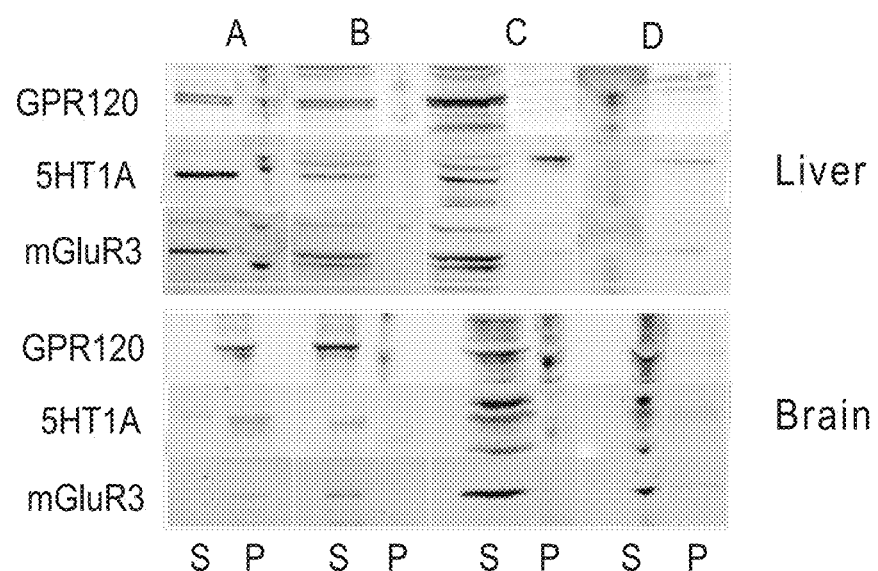
FIG. 4B shows a western blot image for different G protein-coupled receptors (Free Fatty Acid Receptor 4 (GPR120), Serotonin Receptor (5HT1A), and Metabotropic Glutamate Receptor 3 (mGluR3) extracted from mouse tissue (liver and brain), using reagents A-D, as described in FIG. 4A. The data show that the GPCR extraction reagent (C) provides improved banding and yield in the soluble fraction (S) when compared to the insoluble pellet (P).

Free Fatty Acid Receptor 4 (GPR120), Serotonin Receptor (5HT1A), Thrombin Receptor (TR) and Metabotropic Glutamate Receptor 3 (mGluR3) were extracted from HeLa and HEK293 human cell lines (FIG. 4A) and mouse liver and brain tissue (FIG. 4B) using ProteoExtract Transmembrane Protein Extraction Kit (TMPEK) with two buffer options (A and B) and whole cell methods (Thermo Scientific RIPA Lysis (D) and GPCR extraction buffer (C)) (25 mM HEPES/1% DDM/0.5% CHAPS/0.2% CHS/150 mM NaCl/16 mM $MgCl_2$/2 mM EDTA/10% glycerol). The GPCR extraction buffer provided improved solubility and yield of receptor, as evidenced by the more intense banding seen in the soluble fraction (S) lanes when compared to the insoluble pellet (P), in both cell and whole tissue methods. Greater than 80% of the targeted receptor was solubilized using the GPCR extraction buffer as determined by densitometry analysis performed using the Thermo Scientific MyImageAnalysis Software.

Example 4

Radioligand Binding Assays

Figure 5:
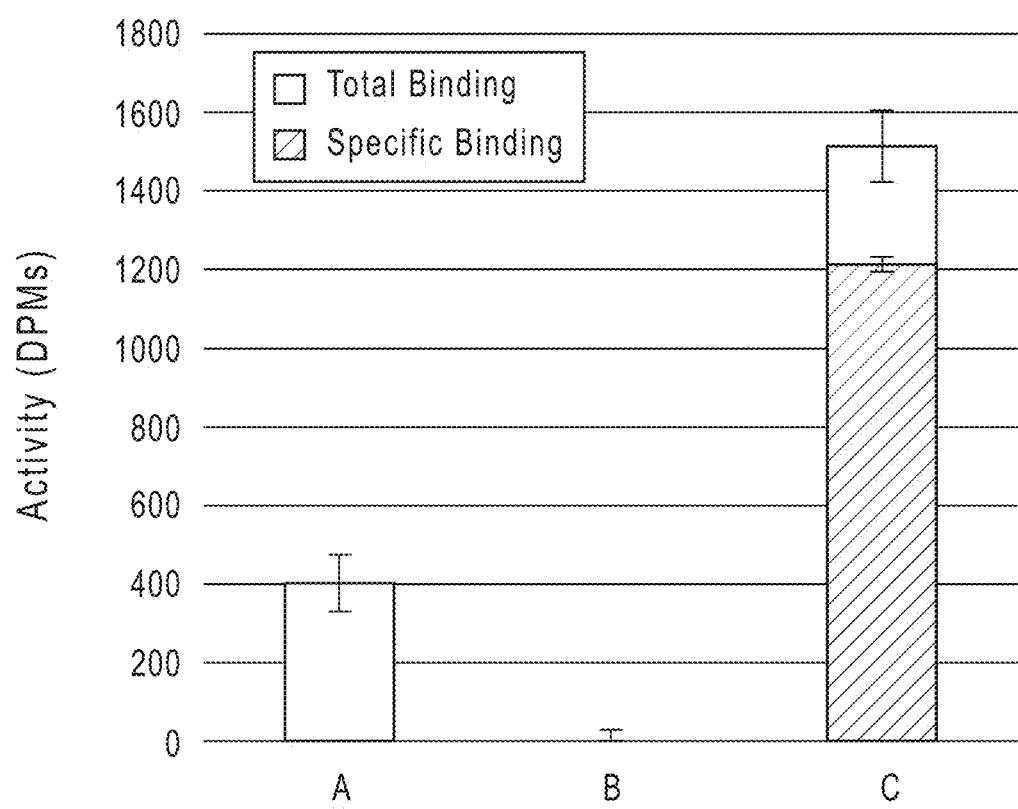
FIG. 5 is a plot showing radioligand binding data for M3 freshly extracted from GeneBLAzer expression cell line using the GPCR extraction reagent (C) and the ProteoExtract Transmembrane Protein Extraction Kit (Millipore) using both buffer options A and B (A and B, respectively). Radioligand binding of the receptor with h3-4DAMP showed that the receptor extracted with a GPCR extraction reagent maintains its function, while the A and B extracts have little to no function.

M3 (Muscarinic Acetylcholine Receptor 3) was extracted from GeneBLAzer M3-NFAT-bla CHO-K1 Cells from Thermo Fisher (Madison, WI) using a GPCR extraction buffer including a cholesterol derivative (C) (25 mM HEPES/1% DDM/0.5% CHAPS/0.2% CHS/150 mM NaCl/16 mM $MgCl_2$/2 mM EDTA/10% glycerol) and the ProteoExtract Transmembrane Protein Extraction Kit using both buffer options (A and B) from MilliporeSigma (St. Louis, MO). A Radioligand Binding Assay was performed on fresh extracts using h3-4DAMP as the radioligand. The data in FIG. 5 demonstrates that extracts prepared using buffer that includes a cholesterol derivative exhibited specific binding of the Muscarinic Acetylcholine Receptor 3 (M3) to h3-4DAMP, while the extracts made with buffer containing no cholesterol derivative (TMPEK A and B) have little to binding at all. Specific binding of ligand to extracted receptor was determined by competition assay with unlabeled ligand as described in the methods section.

Figure 6:
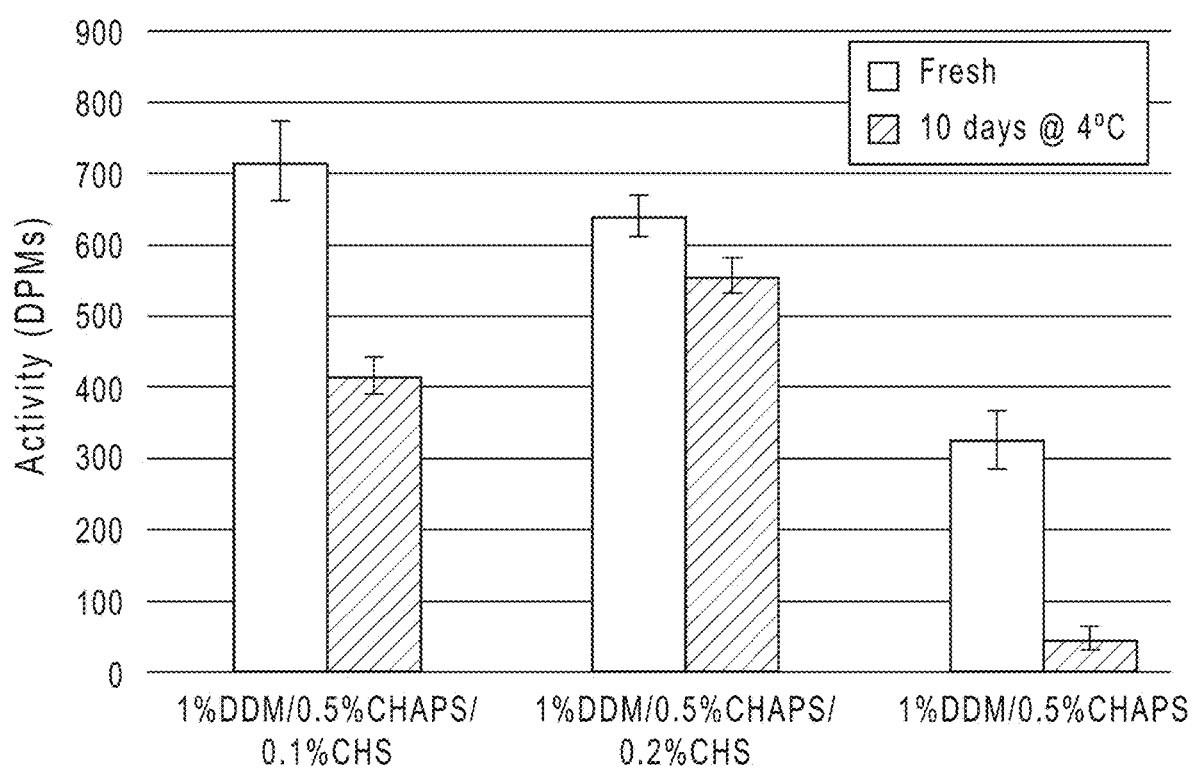
FIG. 6 is a plot showing radioligand binding data for freshly extracted M3 and extracts stored at 4° C. for 10 days with varying amounts of CHS (0%; 0.1%; and 0.2% w/v) in the extraction buffer formulation. Comparison of the radioligand binding data for the three extracts shows that >75% of the receptor's function is maintained when the extracts are stored at 4° C. for 10 days in the presence of 0.2% (w/v) CHS.

FIG. 6 shows data that compares the effect of altering the ratio of detergent to cholesterol derivative in a Radioligand Binding Assay. M3 was extracted from the GeneBLAzer M3-NFAT-bla CHO-K1 cells using buffers made with 0%; 0.1% and 0.2% (w/v) CHS and stored at 4° C. for 10 days. The assay was performed on the stored extracts and directly compared to freshly extracted M3. The buffers including 1% DDM/0.5% CHAPS/0.1% CHS and 1% DDM/0.5% CHAPS/0.2% CHS showed comparable activity for fresh extracts. Activity of fresh extract when CHS is present in the buffer formulation was at least two times greater than that of the receptor extracted using the buffer without CHS, for both CHS concentrations tested. However, when comparing receptor stability post extraction after 10 days storage at 4° C., the sample made using 0.2% CHS exhibited >85% function, whereas the sample prepared using 0.1% CHS exhibited only 60% function. This significant difference in functional activity was surprising given the modest difference in CHS concentration used in the formulations.

Figure 7:
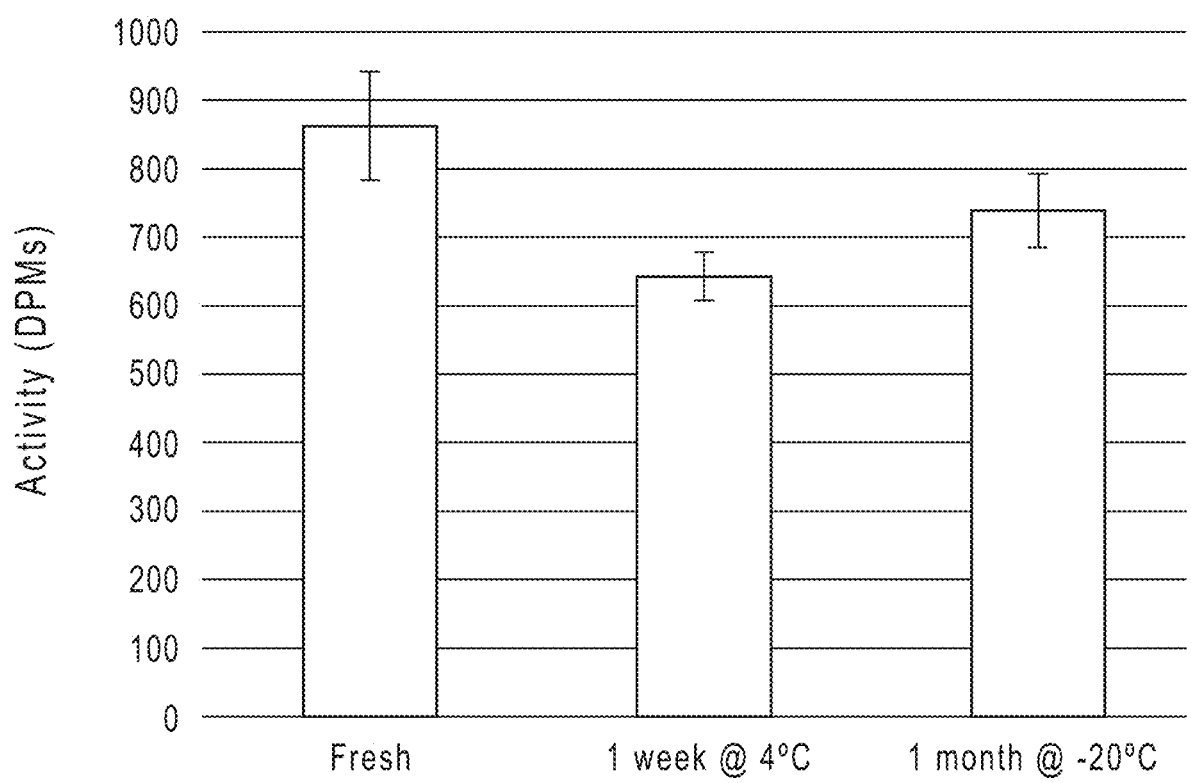
FIG. 7 is a plot showing radioligand binding data for freshly extracted M3 and extracts stored at 4° C. for 1 week and −20° ° C. for 1 month. M3 was extracted from GeneBLAzer expression cell line using the GPCR extraction reagent. Comparison of the radioligand binding data for the three extracts shows that >75% of the receptor's function is maintained when the extracts are stored at 4° C. for 1 week and −20° C. for 1 month.

The stability of extracted M3 was evaluated using different storage conditions. M3 was extracted from the GeneBLAzer M3-NFAT-bla CHO-K1 cells using a GPCR extraction buffer including greater than 0.1% (w/v) CHS and stored at 4° C. for 1 week and −20° C. for 1 month. A Radioligand Binding Assay was performed on the stored extracts and directly compared to freshly extracted M3. Comparison of the three extracts shows that ≥75% of the receptor function is maintained when the extracts were stored at 4° C. for 1 week and −20° C. for 1 month (see, FIG. 7). The increased stability of extracted receptor greatly out performs previously reported stability shown with membrane extraction buffers using 0.1% or less (w/v) CHS.

Example 5

Preparation of Bulk Extraction Buffer

Figure 8:
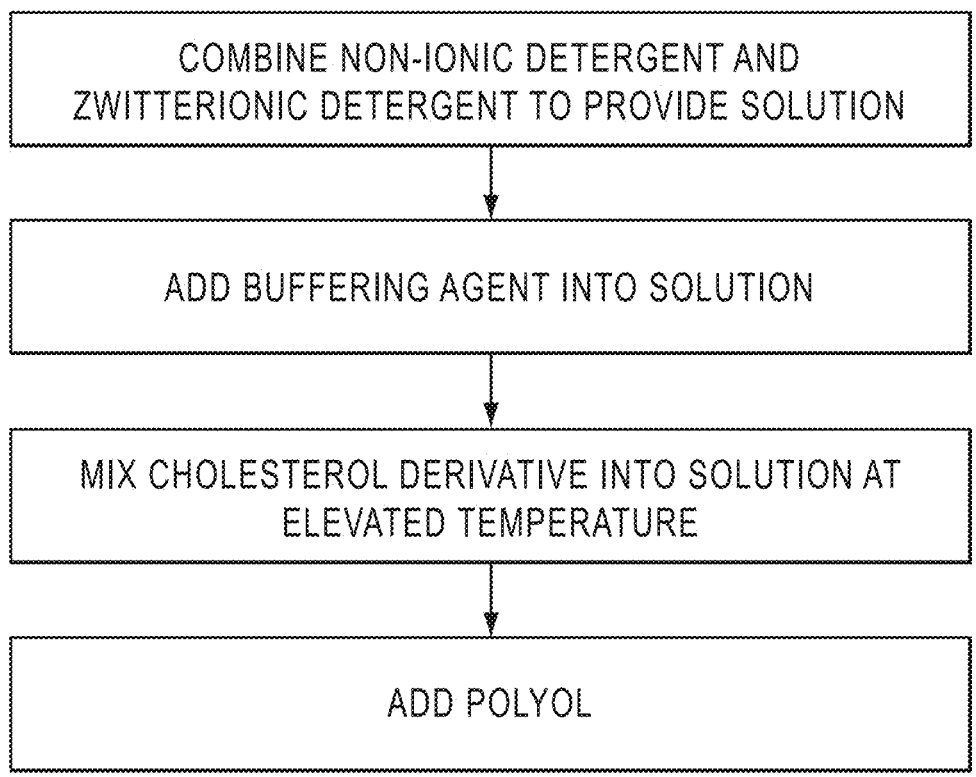
FIG. 8 is a flowchart showing an exemplary method for the preparation of a GPCR extraction reagent.
Figure 9:
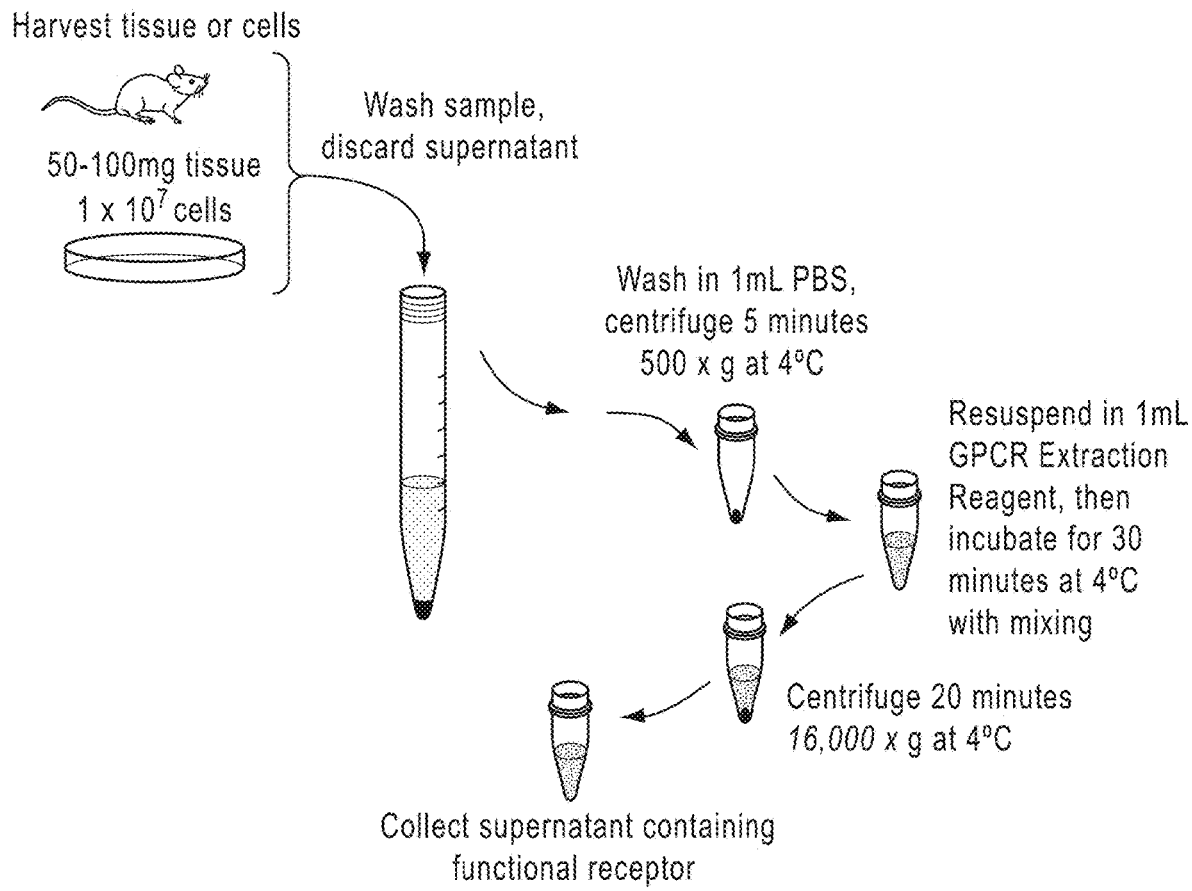
FIG. 9 is a diagram showing a method of using the GPCR formulation for the extraction of GPCRs from tissues or cells.

Extraction reagents were prepared using the detergents, stabilizers, pH and solubilization methods listed in Table 1 and manufacturability of the bulk buffer (e.g., 0.1 L to 10 L) and buffer prepared at R&D scale (e.g., 10-50 mL) were compared. Manufacturability was assessed based on the solubility of cholesterol derivative and its preservation in solution over time. Referring to Table 1, "Good" indicates that the cholesterol derivative dissolved into and remained in solution upon storage. "Poor" indicates that the cholesterol derivative was either not successfully solubilized or did not remain in solution over time. Manufacturability was determined by visual inspection. FIG. 8 is a flow chart illustrating the steps involved in a representative method for the preparation of a bulk extraction buffer using a combination of mixing and heating. Referring to the steps in FIG. 8, polyol can be added after the cholesterol derivative is fully in solution. Typically, the solution containing solubilized cholesterol derivative is removed from the heating source and slightly cooled before polyol is added into the solution. R&D scale buffer formulations were prepared using the same concentration of components as used to prepare the bulk formulation. The detergent(s) were dissolved in solution and then buffering agent was added to adjust the pH of the formulation. The cholesterol derivative then was added, but in lieu of mixing and heating, the formulation was probe sonicated at 100% until the cholesterol derivative was determined to be in solution via visual inspection.

TABLE 1

| SAMPLE | DETERGENT(S) | STABILIZER(S) | PH | SOLUBILIZATION METHOD | MANUFACTURABILITY R&D Scale | MANUFACTURABILITY Bulk Scale |
|---|---|---|---|---|---|---|
| 1 | MNG-3 | polyol/cholesterol derivative | 6, 7 | Sonication | Good | NA |
| 2 | FC-14 | polyol/cholesterol derivative | 6, 7 | Sonication | Good | NA |
| 3 | DDM | polyol/cholesterol derivative | 6, 7, 8 | Sonication | Good | Poor |
| 4 | CHAPS | polyol/cholesterol derivative | 6, 7, 8 | Sonication | Good | Poor |
| 5 | DDM/CHAPS | polyol/cholesterol derivative | 6, 7, 8 | Sonication | Good | Poor |
|   |   |   |   | Heating | Good | Good |
|   |   |   |   | Organic solvent | Good | Good |
| 6 | DDM/CHAPS | cholesterol derivative | 6, 7, 8 | Sonication | Good | Poor |
|   |   |   |   | Heating | Good | Poor |
|   |   |   |   | Organic solvent | Good | Good |

As indicated in Table 1, sonication of solutions that included a cholesterol derivative did not effectively solubilize the cholesterol derivative when the formulation was prepared at bulk scale, even with the addition of polyol and/or CHAPS. Adjusting the pH did not alter manufacturability for the samples tested, although pH 7-7.5 was determined optimal for extraction efficiency across multiple cell lines and targets. Organic solvents were shown to improve solubility of the cholesterol derivative (see, Sample 5 and Sample 6), which was advantageous for scalability, but use of organic solvents in the formulation had negative downstream effects on the stability of the extracted receptor (data now shown). Interestingly, the formulation that did not include polyol did not exhibit good bulk scale manufacturability (see, Sample 6), suggesting that polyol is important to maintain dissolution of the cholesterol derivative over time. Of the samples tested, Sample 5 provided optimal bulk scale manufacturability and was tested using Western blot and functional radioligand binding assays to confirm functional performance, as described in Example 3 and Example 4. The formulation of Sample 5 was successfully prepared at 1 L, 10 L and 20 L volumes. The functional results for the formulations prepared at bulk scale (i.e., 0.1 L-20 L) indicated that extraction and stabilization performance properties were maintained, making these formulation particularly useful for bulk manufacturing of buffers for the processing of GPCR containing samples.

Example 6

Extraction of GPCRs from Cells and Tissues

1×10⁷ cultured cells or 50-100 mg of tissue are washed in PBS, subsequently lysed in 1 mL extraction reagent, as disclosed herein, and incubated for 30-60 minutes at 4° C. After incubation, samples are centrifuged at 16,000×g for 20 minutes. The supernatant containing the solubilized protein is collected. The amount of solubilized protein can be measured using a BCA Assay Kit (Thermo Fisher Scientific)

Example 7

Purification of GPCR from Over-Expression System

Figure 10:
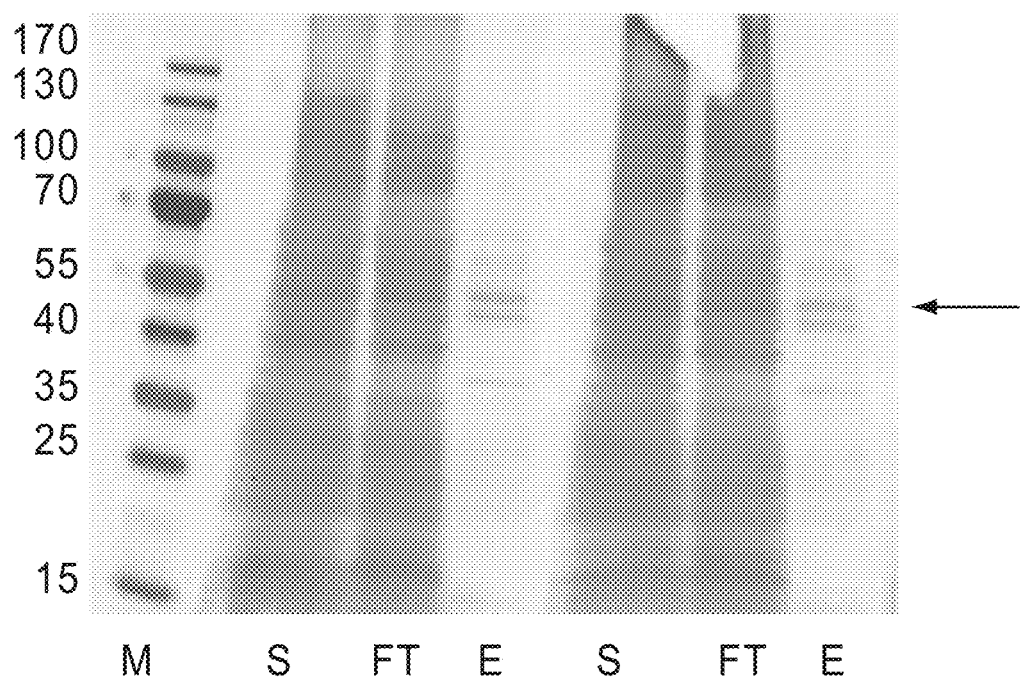
FIG. 10 is silver-stained gel electrophoresis image comparing whole cell lysate to purified eluate for A2AR-GFP-His receptor stabilized in vesicles using the extraction and stabilization reagents described herein. Duplicate runs were performed for a whole cell lysate containing expressed A2AR-GFP-His receptor. The starting sample (S) was incubated in the presence of Thermo Scientific™ Pierce™ Ni-NTA Magnetic Agarose Beads. The unbound components in the flow through (FT) were compared to eluate (E) and a protein sizing ladder (M). The arrow identifies the band in the gel image for a component having a MW corresponding to that of the target receptor of interest.

100 µL of Pierce™ Ni-NTA Magnetic Agarose Beads (Product no. 78605; Rockford, IL) at a 25% slurry was pipetted into a 1.5 mL microcentrifuge tube for each sample. The beads were washed twice with 500 µL of cold Equilibration Buffer (25 mM HEPES, 0.3 M NaCl, 10 mM imidazole, mixed 9:1 with extraction reagent as disclosed herein, pH 8.0). 1 mL of protein extract prepared as described in Example 6 diluted to 1 mg/mL with Equilibration Buffer was added to the washed beads, vortexed for 10 seconds and then mixed on an end-over-end rotator for 60 minutes at 4° C. After incubation, the beads were collected on a magnetic stand and the supernatant was saved (flow-through) for downstream analysis. Next the beads with the bound A2AR-GFP-His was washed twice with 500 µL of Wash Buffer (25 mM HEPES, 0.3 M NaCl, 15 mM imidazole, mixed 9:1 with extraction reagent, pH 8.0). 250 µL of Elution Buffer (25 mM HEPES, 0.3 M NaCl, 0.3 M imidazole, mixed 9:1 with extraction reagent, pH 8.0) to the washed beads and then mixed on an end-over-end rotator for 10 minutes at room temperature. Beads were then collected on a magnetic stand, and the eluate containing A2AR-GFP-His was carefully removed. Samples were either directly analyzed by SDS-PAGE and Silver Stain or buffer exchanged into the full strength extraction reagent using Thermo Scientific™ Zeba™ Spin Desalting Columns for overnight storage at 4° C. before proceeding to radio-ligand binding assays. The gel image for purified A2AR-GFP-His shows efficient binding and elution of the receptor from the Ni-NTA magnetic agarose beads (see, FIG. 10). Silver stain was used to reveal the purity and residual contaminants remaining in the sample. Similar results were seen with an adenosine receptor construct in Expi293 cells expressing A2AR-GFP-His and lysed using the GPCR Extraction and Stabilization Reagent when extracts were purified using Pierce™ Ni-NTA Magnetic Agarose as described above. Samples were eluted with 0.3M imidazole, pH 8.0 and analyzed by western blot using three different primary antibodies for detection (1=anti-A2AR, 2=anti-6×His, 3=anti-GFP). Start, unbound, and elution fractions showed effective capture and elution of the 6×His tagged adenosine receptor type 2A and confirms the results obtained in the silver stain gel assay (data not shown).

Figure 11:
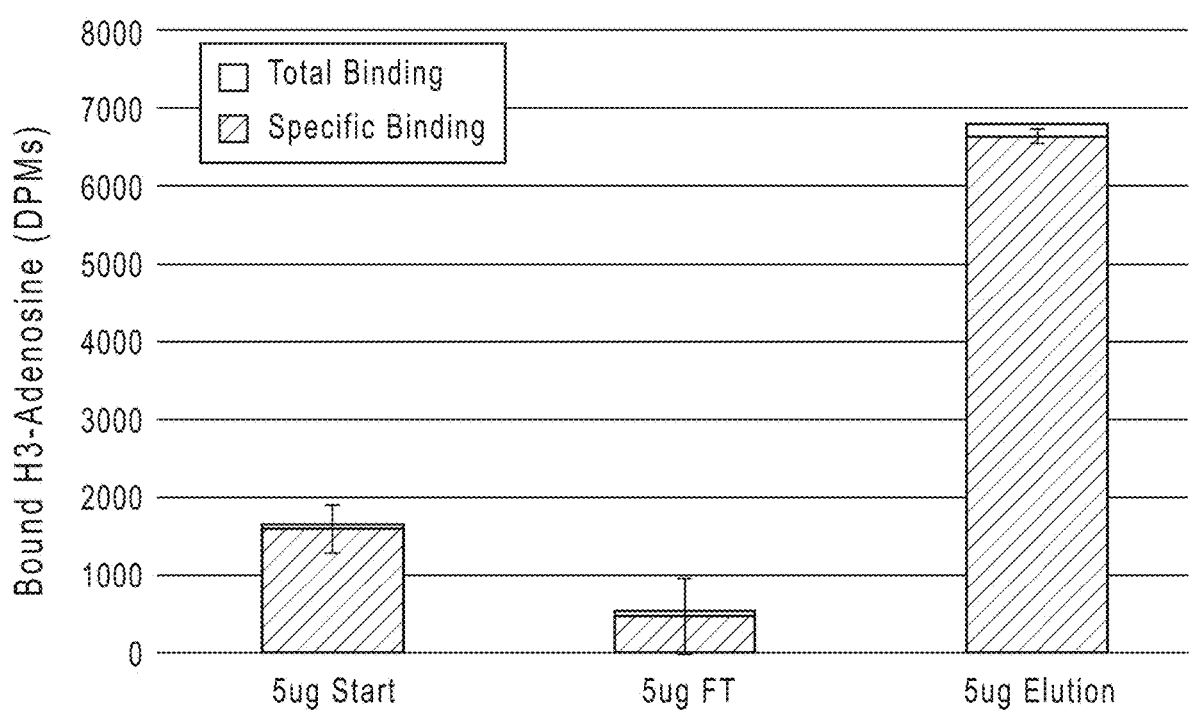
FIG. 11 is a bar graph for a radioligand binding experiment showing that A2AR-GFP-His activity is greatly enriched by affinity purification. The graph plots disintegrations per minute for H3-adenosine bound to the A2AR-GFP-His for 5 μg of starting sample prior to purification (Start), unbound components in the flow through (FT) and eluate (Elution) after purification with Ni-NTA Magnetic Agarose Beads.

Total and specific binding of active A2AR-GFP-His receptor was assessed using a radioligand binding assay (see, FIG. 11). The data shows that adenosine binding activity was retained throughout the purification and that the A2AR specific binding activity was significantly enhanced in the purified/eluted fraction. Further, it was found that functional activity for the receptor was maintained during the purification process and that active protein can be maintained throughout the purification workflow by keeping the GPCR extraction and stabilization reagent at the critical micelle concentration (e.g., 1/10 strength into purification buffers).

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

All of the U.S. patents, U.S. patent application publications, U.S. patent applications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

What is claimed is:

1. A bulk scale solution comprising a solubilized cholesterol derivative, comprising:
   a maltoside-based non-ionic detergent;
   a zwitterionic detergent;
   a buffering agent, wherein the buffering agent is HEPES (4-(2-hydroxyethyl)-1-piperazineethanesulfonic acid), MOPS (3-(N-morpholino)propanesulfonic acid), MES (2-(N-morpholino)ethanesulfonic acid), HEPPs, or PIPES (piperazine-N,N'-bis(2-ethanesulfonic acid));
   10-20% (w/v) of a polyol; and
   about 0.15 to 0.3% (w/v) of a cholesterol derivative, wherein the concentration ratio (w/v) of the cholesterol derivative to total detergent is about 0.5 or less, and wherein the solution is at a pH of 5-8, and wherein the cholesterol derivative remains solubilized in the bulk scale solution, wherein the bulk scale solution has a volume of about 1 L to about 20 L.

2. A method of extracting a membrane protein from a cell or a tissue, comprising:
   providing a sample comprising a cell or a tissue; and
   incubating the sample in the solution of claim 1, wherein the solution is in an amount sufficient to extract the membrane protein from the cell or tissue, and wherein the extracted membrane protein is solubilized in the solution.

3. The method of claim 2, wherein the membrane protein is a G-protein coupled receptor (GPCR), and wherein the solubilized GPCR maintains functional integrity.

4. The method of claim 3, wherein greater than 70% of the function of the GPCR is maintained when stored for 7 days at 4° C. or wherein greater than 70% of the function of the GPCR is maintained when stored for 1 month at −20° C.

5. A kit for extracting a GPCR from a cell or tissue, comprising:
   a) a GPCR extraction solution, comprising:
      a maltoside-based non-ionic detergent;
      a zwitterionic detergent;
      a buffering agent, wherein the buffering agent is HEPES (4-(2-hydroxyethyl)-1-piperazineethanesulfonic acid), MOPS (3-(N-morpholino)propanesulfonic acid), MES (2-(N-morpholino)ethanesulfonic acid), HEPPs, or PIPES (piperazine-N,N'-bis(2-ethanesulfonic acid));
      10-20% (w/v) of a polyol; and
      about 0.15 to 0.3% (w/v) of a cholesterol derivative, wherein the concentration ratio (w/v) of the cholesterol derivative to total detergent is about 0.5 or less, and wherein the solution is at a pH of 5-8, and wherein the cholesterol derivative remains solubilized in the solution; and
   b) instructions for extracting the GPCR from the cell or tissue.

6. A method for preparing a solution in bulk scale according to claim 1, wherein the solution comprises solubilized cholesterol derivative, comprising:
   combining the maltoside-based non-ionic detergent and the zwitterionic detergent to provide a solution at a first temperature;
   adding the buffering agent into the solution;
   elevating the temperature of the solution to a second temperature, wherein the second temperature is greater than the first temperature;
   mixing the cholesterol derivative into the solution at the second temperature; and
   adding the polyol into the solution to provide the bulk scale solution, wherein the bulk scale solution is buffered to pH 5-8, and wherein the cholesterol derivative is solubilized in the bulk scale solution.

7. The method of claim 6, further comprising returning the bulk scale solution to a third temperature that is less than the second temperature, wherein the cholesterol derivative is solubilized in the bulk scale solution at the third temperature.

8. The solution of claim 1, wherein the non-ionic detergent is selected from n-dodecyl-b-D-maltopyranoside, n-octyl-β-D-maltopyranoside, n-hexyl-β-D-maltopyranoside, glyco-diosgenin, lauryl maltose neopentyl glycol, and maltose neopentyl glycol.

9. The solution of claim 1, wherein the zwitterionic detergent is 3-[(3-cholamidopropyl)dimethylammonio]-1-propanesulfonate (CHAPS), cocamidopropyl hydroxysultaine, cocamidopropyl betaine, phospholipids, phosphatidylethanolamine, or phosphatidylcholine.

10. The solution of claim 1, wherein the cholesterol derivative is an acidic cholesterol ester.

11. The solution of claim 1, wherein the cholesterol derivative is selected from cholesteryl hemisuccinate (CHS), cholesterol α-D-glucopyranosyl-(1→4)-β-D-glucopryanoside, and 5,11,17-tris[(carboxy)methyl]-25-monomethoxy-triazolo-(3α-cholesteryl)-26,27,28-trihydroxycalix[4]arene.

12. The solution of claim 1, wherein the polyol is glycerol, sorbitol, or xylitol.

13. The solution of claim 1, wherein the solution is at a pH of 7-7.5.

14. A solution comprising a solubilized cholesterol derivative, wherein the solution comprises:
   a maltoside-based non-ionic detergent;
   a zwitterionic detergent;
   a buffering agent, wherein the buffering agent is HEPES (4-(2-hydroxyethyl)-1-piperazineethanesulfonic acid), MOPS (3-(N-morpholino)propanesulfonic acid), MES (2-(N-morpholino)ethanesulfonic acid), HEPPs, or PIPES (piperazine-N,N'-bis(2-ethanesulfonic acid));
   10-20% (w/v) of a polyol; and
   about 0.15 to 0.3% (w/v) of a cholesterol derivative, wherein the concentration ratio (w/v) of the cholesterol derivative to total detergent is about 0.5 or less, and wherein the solution is at a pH of 5-8, wherein the cholesterol derivative remains solubilized in the solution.

15. The solution of claim 14, wherein the non-ionic detergent is selected from n-dodecyl-b-D-maltopyranoside, n-octyl-β-D-maltopyranoside, n-hexyl-β-D-maltopyranoside, glyco-diosgenin, lauryl maltose neopentyl glycol, and maltose neopentyl glycol.

16. The solution of claim 14, wherein the zwitterionic detergent is selected from 3-[(3-cholamidopropyl)dimethylammonio]-1-propanesulfonate (CHAPS), cocamidopropyl hydroxysultaine, cocamidopropyl betaine, phospholipids, phosphatidylethanolamine, and phosphatidylcholine.

17. The solution of claim 14, wherein the cholesterol derivative is selected from cholesteryl hemisuccinate (CHS), cholesterol α-D-glucopyranosyl-(1→4)-β-D-glucopryanoside, and 5,11,17-tris[(carboxy)methyl]-25-monomethoxy-triazolo-(3α-cholesteryl)-26,27,28-trihydroxycalix[4]arene.

18. The solution of claim 14, wherein the polyol is glycerol, sorbitol, or xylitol.

19. A method of extracting a membrane protein from a cell or a tissue, comprising:

provising a sample comprising a cell or a tissue; and incubating the sample in the solution of claim 14, wherein the solution is in an amount sufficient to extract the membrane protein from the cell or tissue, and wherein the extracted membrane protein is solubilized in the solution.

20. The method of claim 19, wherein the non-ionic detergent is selected from n-dodecyl-b-D-maltopyranoside, n-octyl-β-D-maltopyranoside, n-hexyl-β-D-maltopyranoside, glyco-diosgenin, lauryl maltose neopentyl glycol, and maltose neopentyl glycol, and wherein the zwitterionic detergent is selected from 3-[(3-cholamidopropyl)dimethylammonio]-1-propanesulfonate (CHAPS), cocamidopropyl hydroxysultaine, cocamidopropyl betaine, phospholipids, phosphatidylethanolamine, and phosphatidylcholine.

* * * * *

UNITED STATES PATENT AND TRADEMARK OFFICE
CERTIFICATE OF CORRECTION

PATENT NO. : 12,123,814 B1
APPLICATION NO. : 16/900019
DATED : October 22, 2024
INVENTOR(S) : Barbara Kaboord et al.

It is certified that error appears in the above-identified patent and that said Letters Patent is hereby corrected as shown below:

On the Title Page

In Column 1, item (54), in title, Line 1, delete "G- PROTEIN" and insert -- G-PROTEIN --, therefor.

In Column 1, item (72), in Inventors, Line 2, delete "Rockton, IL" and insert -- Rockford, IL --, therefor.

In Column 1, item (72), in Inventors, Line 3, delete "Rockton, IL" and insert -- Rockford, IL --, therefor.

In the Specification

In Column 1, Line 1, delete "G- PROTEIN" and insert -- G-PROTEIN --, therefor.

In the Claims

In Column 20, Claim 8, Line 35, delete "-b-" and insert -- -β- --, therefor.

In Column 20, Claim 11, Lines 48-49, delete "glucopryanoside," and insert -- glucopyranoside, --, therefor.

In Column 21, Claim 15, Line 5, delete "-b-" and insert -- -β- --, therefor.

In Column 21, Claim 17, Lines 15-16, delete "glucopryanoside," and insert -- glucopyranoside, --, therefor.

In Column 22, Claim 20, Line 11, delete "-b-" and insert -- -β- --, therefor.

Signed and Sealed this
Eighteenth Day of February, 2025

Coke Morgan Stewart
*Acting Director of the United States Patent and Trademark Office*